US007160506B2

(12) United States Patent
Deshpande

(10) Patent No.: US 7,160,506 B2
(45) Date of Patent: Jan. 9, 2007

(54) ELECTRONIC DISINFECTION OF AIRBORNE POLLUTANTS

(75) Inventor: Deepak Anant Deshpande, Katy, TX (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 11/011,627

(22) Filed: Dec. 14, 2004

(65) Prior Publication Data

US 2006/0127270 A1 Jun. 15, 2006

(51) Int. Cl.
*A61L 2/00* (2006.01)

(52) U.S. Cl. ..................... 422/4; 96/28; 96/223; 422/1; 422/120; 422/121; 422/122; 422/186; 422/186.04

(58) Field of Classification Search .................... 422/1, 422/4, 22, 120, 121, 122, 186, 186.04; 96/28, 96/223

See application file for complete search history.

(56) References Cited

U.S. PATENT DOCUMENTS

| | | | | |
|---|---|---|---|---|
| 4,532,372 | A * | 7/1985 | Nath et al. | 136/256 |
| 5,356,484 | A * | 10/1994 | Yater et al. | 136/200 |
| 5,656,063 | A * | 8/1997 | Hsu | 95/58 |
| 6,245,132 | B1 * | 6/2001 | Feldman et al. | 96/28 |
| 6,645,778 | B1 * | 11/2003 | Ahn | 438/3 |

* cited by examiner

*Primary Examiner*—Krisanne Jastrzab
(74) *Attorney, Agent, or Firm*—Akerman Senterfitt; Neil R. Jetter

(57) ABSTRACT

A system for electronically disinfecting air includes a first electrode, at least a second electrode, the first and second electrode being spaced apart from one another. The surfaces of the first or second electrode include a semiconductor or a dielectric layer having a thickness of at least 10 angstroms disposed thereon. An electrical power supply is connected between the first and said second electrode, wherein pollutants in air to be disinfected are destroyed by exposure of the air to surfaces of the first or second electrode.

20 Claims, 6 Drawing Sheets

ELECTRONIC DISINFECTION OF AIRBORNE POLLUTANTS

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The invention relates to systems and methods for disinfecting fluids using electronically biased surfaces.

BACKGROUND

Several microbiological particle control systems exist. Mechanical and electronic filters can be used to reduce indoor concentrations of respirable particles, such as in a forced air heating/cooling system of a building. Microbiological filters have been used for disinfection of air and other gases because of their low cost and ease of handling. These filters can be constructed to remove not only microorganisms, but also submicron particles as well. For efficient and economic operation of these filters, the aerosol content of the air to be filtered must be low, where the term "aerosols" generally refers to microorganisms, particles, and droplets of liquid dispersed in air. A disadvantage of such filters is that they do not permanently remove the contaminants, but just transfer them to the filter medium. Clogging of the filter medium can result which can cause high pressure drops. In addition, microorganisms trapped on the filter media continue to multiply making the filter media a breeding ground and thus hazardous.

Another method of microbiological particle removal is UV disinfection. UV disinfection has been widely used to destroy biological contaminants and toxic chemicals. Such UV treatment has worked well for disinfection, but the indoor environment may also be contaminated with low level toxic chemicals such as formaldehyde, styrene, and toluene. Ultraviolet energy alone has proven generally ineffective in degrading these chemicals.

Another alternative that has gained increasing attention is photocatalytic oxidation (PCO), which involves the use of a photocatalyst such as $TiO_2$ for the destruction of hydrocarbons and microorganisms in fluids. Titanium dioxide ($TiO_2$) is a semiconductor photocatalyst with a room temperature band gap energy of about 3.2 eV. When this material is irradiated with photons having wavelengths less than about 385 nm (UV), the band gap energy is exceeded and electrons are generated through promotion from the valence band to the conduction band which results in the generation of holes (h+). The resulting highly reactive electron-hole pairs have lifetimes in the space-charge region of the photocatalyst that enables participation in chemical reactions, provided recombination events do not occur first. The most widely postulated chemical reactions are shown below:

$OH^{-}+h+\rightarrow OH$ (hydroxyl radical)

$O_2+e-\rightarrow O_2^{-}$(super-oxide ion)

Hydroxyl radicals and super-oxide ions are highly reactive species that can readily oxidize volatile organic compounds (VOCs) adsorbed on catalyst surfaces. They can also kill and oxidize adsorbed bioaerosols. The process is a form of heterogeneous photocatalysis, or more specifically PCO.

Several attributes of PCO make it a strong candidate for indoor air quality applications. Pollutants, particularly VOCs, are preferentially adsorbed on photocatalytic surfaces and oxidized primarily to carbon dioxide ($CO_2$). Thus, rather than simply changing the phase and concentrating the contaminant, the absolute toxicity of the treated air stream is reduced, allowing the photocatalytic reactor to operate as a self-cleaning filter.

Photocatalytic reactors may be integrated into new and existing heating, ventilation, and air conditioning (HVAC) systems due to their modular design, room temperature operation, and generally negligible pressure drop. These attributes contribute to the potential of PCO technology to be an effective process for removing and destroying low level pollutants in indoor air, including bacteria, viruses and fungi.

For example, U.S. Pat. No. 5,933,702 Goswami discloses a method for disinfecting an air stream containing microorganisms. The method includes the steps of providing an air stream containing microorganisms having a relative humidity greater than about 40% and contacting the air stream with a photocatalyst having a predetermined band gap energy in the presence of a source of photons having a wavelength corresponding to the band gap energy of the photocatalyst. At least a portion of the microorganisms in the air stream are destroyed by photocatalytic oxidation. Improved devices embodying the method of the invention are disclosed, such as stand-alone devices and devices incorporated into the HVAC systems of buildings, including the air supply registers. Photocatalyst-coated filter media capable of trapping bioaerosols are also disclosed.

The photocatalytic process is energy intensive because of the very low absorption rate of light by the photocatalyst. Accordingly, the light radiation flux required at the photocatalyst surface needs to high and most of the light energy is not utilized for the disinfection process.

Further, only the exterior surface of the photocatalyst, participates in the destruction processes. This area could be much smaller than area of the substrate on which the photocatalyst is deposited. The low light absorption and low disinfection area leads to a low destruction rate and high power consumption for the photocatalytic disinfection process. The low destruction rate also results into slow regeneration of the fouled photocatalyst. In addition, photocatalytic processes are made further inefficient due to hole-electron recombination of a portion of the photogenerated holes and electrons.

SUMMARY

A system for electronically disinfecting air includes a first electrode, at least a second electrode, the first and second electrode being spaced apart from one another. The surfaces of the first and/or second electrode include a semiconductor or a dielectric layer having a thickness of at least 10 angstroms disposed thereon. An electrical power supply is connected between the first and said second electrode, wherein pollutants in air to be disinfected are destroyed by exposure of the air to surfaces of the electrodes. The dielectric or semiconductor thickness can be from 20 angstroms to 20 microns, such as 20 to 100 angstroms.

The first and second electrodes comprise aluminum and the dielectric layer aluminum oxide. The first and said second electrode can be arranged to form a capacitor. In one configuration, a plurality of capacitors are arranged in a stacked configuration.

The electrodes can have surface roughness. Surface roughness provides an increase in surface area. As used herein, the phrase "surface roughness" corresponds to a surface having a minimum arithmetical average roughness of at least 0.1 microns.

The first electrode can be disposed outside a path of the air to be disinfected and connected to ground, while the second electrodes can be disposed in a path of the air to be disinfected. A stacked electrode configuration can be used in this embodiment.

An electric field at surfaces of the first and/or second electrode under bias from the power supply is preferably less than 2.7 MV/m. This level can eliminate, or at least significantly reduce ionization of the air. At least one electrode can be porous or include holes formed therein to allow air to pass through. The power supply can be an AC supply or a DC supply.

A method for electronically disinfecting air comprising the steps of providing at least one dielectric or semiconductor coated electrical conductive surface, the electrically conductive surface having a dielectric or semiconductor coating thereon having a thickness of at least 10 angstroms, biasing the dielectric or semiconductor coated electrical conductive surface to impose charges on the electrically conductive surface. Air to be disinfected is passed over the dielectric or semiconductor coated electrical conductive surface, wherein pollutants in the air are destroyed by exposure to the dielectric or semiconductor coated electrically conductive surface. The method can further comprise the step of heating the dielectric or semiconductor coated electrically conductive surface to regenerate the surface by removing material disposed thereon.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

Figure 1:
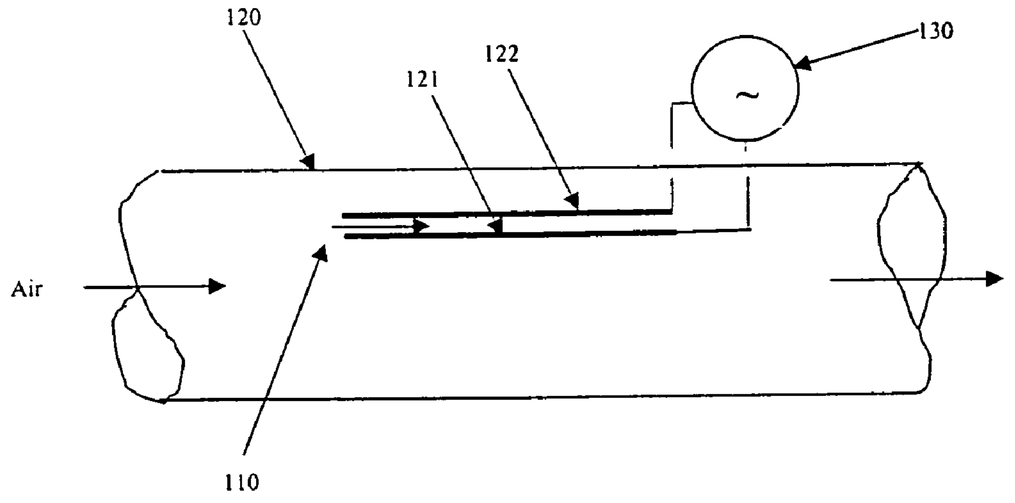
FIG. 1 shows a simplified system for electronically disinfecting air using a capacitive arrangement, according to an embodiment of the invention.

A system for electronically disinfecting air includes a first electrode, at least a second electrode, the first and second electrode being spaced apart from one another. The first and second electrodes can be covered with a dielectric or a semiconducting layer. The dielectric or semiconductor layer thickness is at least 1 nm, and is generally in a range from 1.5 to 10 nm, such as 2 nm, 3 nm, 4 nm, 5 nm, 6 nm, 7 nm, 8 nm, or 9 nm. Dielectrics in this thickness range can be formed from exposure of some metals to ambient air. However, the dielectric or semiconductor thickness can be greater than 10 nm, such as up to several Elms in thickness. In the case of semiconductor layers or dielectric layers of thickness at least about 10 nm, deposition techniques, such as chemical vapor deposition, may generally be used.

In a preferred embodiment, an electrical power supply is connected between the first and second electrodes which are arranged to form a capacitor, which imposes opposite charges on the two electrodes. Airborne pollutants are destroyed and the air disinfected by exposure of the air to be disinfected to the surfaces of these electrodes. As used herein, the word "exposure" is defined as proximity to the charged electrode surface sufficient for the electric field emanating from or terminating on the charged surface to destroy at least a portion of the pollutant, or physical contact with the charged surface. The electrical power supply voltage for biasing the electrodes is preferably limited so that the resulting electric field is insufficient to ionize the air to be disinfected, or at least low enough to reduce ionization of the air to a very low level.

The pollutants can include particulates, viruses and organisms including biohazardous microorganisms, allergens, as well as certain volatile organic compounds (VOCs). The system can include a blower or other suitable structure to propel air to be disinfected toward the electrodes provided. Air flow induced by thermal convection or natural draft can also be disinfected.

The electrodes can take on a variety of forms and shapes. Some of the shapes can include flat, cylindrical, spherical, conical, pointed or a combination thereof. The surfaces may be in the form of plates, nets, meshes, porous media or their combinations. When a capacitor arrangement is used, the capacitor can utilize parallel surfaces, concentric surfaces, skewed surfaces, or combinations thereof.

In a preferred embodiment, the electrode surface has surface roughness defined above as a surface having an arithmetical average roughness of at least 0.1 microns. When dielectric coated electrodes are used, such as aluminum oxide coated aluminum electrodes, the roughness generally extends into the dielectric coating. Some exemplary methods for generating surface roughness are grinding, sandblasting, machining, cold rolling, and hot rolling. In the case of grinding, the coarser the grit being used, the rougher the sample surface will be. Alternatively, the specified roughness may be inherently present on a sheet coming out of the rolling mill. Arithmetical average roughness values can be determined using a device having a fine stylus that is moved over the surface to be tested.

The air flow pattern with respect to the electrodes may be along the electrode surfaces, impinging on the electrode surfaces, through the electrodes, or combination of any of these. Electrodes can include holes formed therein having sufficient size to allow air passage therethrough without significant pressure drop, but preferably small enough to trap most biohazards when a flow through arrangement is utilized. Alternatively, electrodes can be formed from porous electrically conductive materials. Electrode holes or porosity increases the exposed surface area and can be used to manipulate the resulting air flow path/pattern.

The system and associated inventive process are simple, low power, low maintenance, and low cost. Such systems do not involve chemicals or nanoparticles, and generally do not require any post disinfection cleanup. The fabrication and operating cost of electronic disinfection systems according to the invention is low because of a simple design with no complex components, and very low power requirements.

FIG. 1 shows an exemplary air disinfecting system 110 installed inside an air duct 120, such as used in a typical HVAC system. Although shown applied to a HVAC system, the system is in no way limited. The invention can be utilized wherever low power air disinfection is desired, such as for stand-alone unit in rooms. System 110 includes a first electrode 121 and second electrode 122 which are spaced apart from one another, to form a capacitor. The single capacitor shown in FIG. 1 will generally not be efficient for trapping particles and/or destroying organisms. A more efficient arrangement is the multi-capacitor arrangement shown in FIG. 3 described below.

The electrode spacing distance is generally selected based on the bias applied to achieve the desired non-ionizing electric field. Although air duct 120 includes a single disinfecting system 110, multiple disinfecting systems can be used, such as at a plurality of locations along the length of a duct.

The electrodes 121 and 122 can be formed from a variety of good electrical conductors, including most metals. Aluminum is a preferred metal due to its low cost and its ability to form a thin dielectric layer upon exposure to the air. Although not shown in FIG. 1, as noted above, the electrode surface can be covered with a dielectric, preferably a dielectric having a relatively high dielectric constant such as aluminum oxide ($Al_2O_3$) or silicon dioxide. Semiconductors including titanium dioxide ($TiO_2$) or Barium Titanate ($BaTiO_3$) may also be used. In one embodiment, the electrodes 121 and 122 are aluminum and have an $Al_2O_3$ dielectric coating.

Electrodes can be formed metals which react readily (oxidize) with oxygen in air, so that under ambient conditions the surface is covered with a thin oxide film. The details of film structure and composition depend on the history of exposure to the ambient atmosphere. For aluminum exposed to ambient conditions, there is always a barrier oxide layer on the metal surface that is about 1 to 3 nm thick. The barrier oxide stabilizes the surface against further reactions with its environment and is an excellent electrical insulator. This oxide is reported to support an electric field (volts/thickness) on the order of 1 V/nm. The aluminum oxide coating can also act as an electrophyllic medium.

A power supply 130 biases electrodes 121 and 122. An AC supply 130 is shown in FIG. 1. The signal frequency can be from about 10 Hz to several kHz. However, a DC supply may also be used. Bias levels generally range from 10 to 120 volts, such as 20, 30, 40, 50 ,60, 70, 80, 90, 100, or 110 volts, preferably being from about 60 to 100 volts. When a dielectric having a thickness more than about 2 to 3 nm coats the electrodes, the dielectric should be absent from the area in which the electrical contact is made to the electrodes to limit contact resistance.

Figure 2:
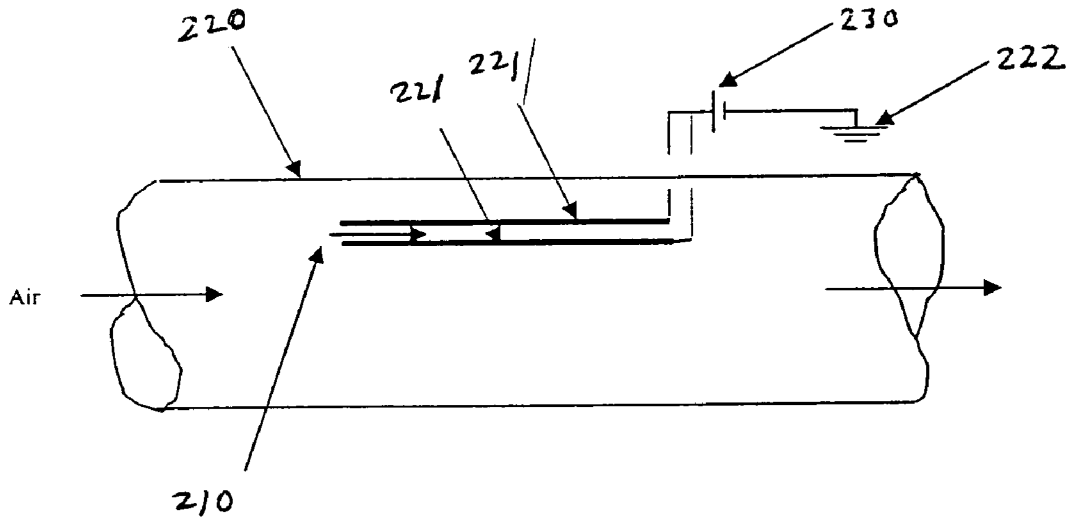
FIG. 2 shows a simplified system for electronically disinfecting air using electrodes biased at the same potential and polarity, according to another embodiment of the invention.

FIG. 2 shows a simplified system for electronically disinfecting air 210, according to another embodiment of the invention. System 210 is installed inside an air duct 220, such as used in a typical HVAC system. As with system 110 shown in FIG. 1, system efficiency is limited by the electrodes acting on only a small percentage of the cross-sectional area of duct 220 but can easily be increased by increasing the number or orientation of the electrodes. System 210 includes a first electrodes 221 and second electrode 222 far removed from first electrode 221. Electrodes 221 are both connected to one terminal (+) of a power supply 230 and spaced apart from one another to provide isolated positively charged surfaces. The negative terminal (−) of power supply 230 is connected to the second electrode 222 which is tied to ground. Although air duct includes a single disinfecting system 210, multiple disinfecting systems can be used, such as stacked in a serial and parallel arrangement (not shown).

Figure 3:
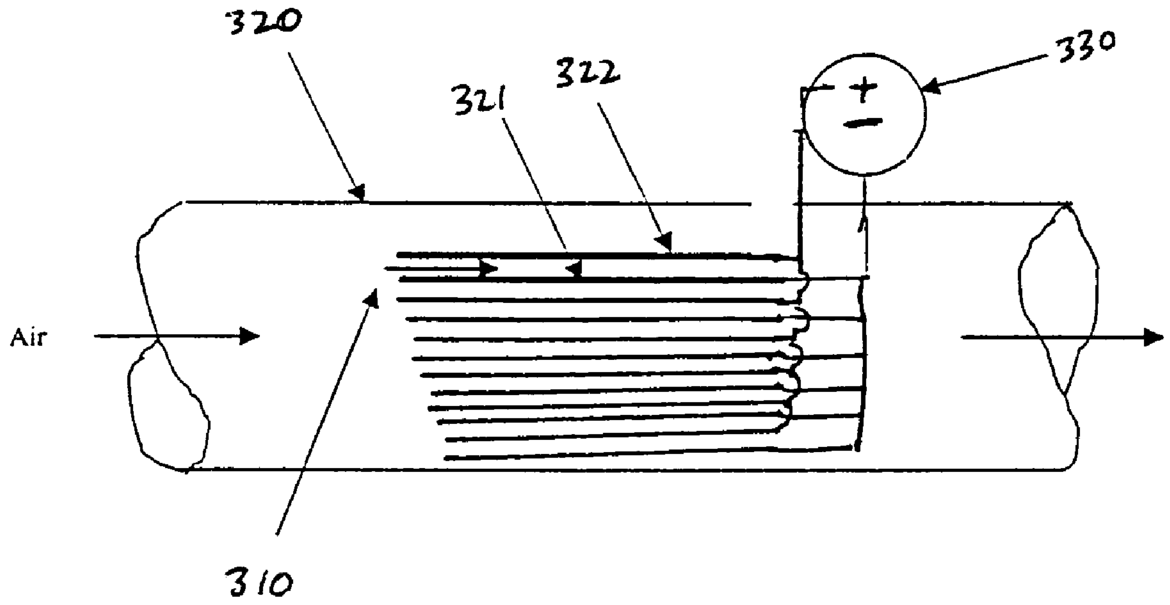
FIG. 3 shows a simplified system for electronically disinfecting air using a stacked multicapacitive arrangement according to yet another embodiment of the invention.

FIG. 3 shows a simplified exemplary system 310 for electronically disinfecting air, according to yet another embodiment of the invention. System 310 is shown installed inside an air duct 320, such as used in a typical HVAC system. System 310 is analogous to system 110 shown in FIG. 1, except the disinfecting surface comprise a plurality of stacked capacitors formed by alternating electrodes 321 and 322. Electrodes 321 are connected to the (−) terminal of power supply 330, while electrodes 322 are connected to the + terminal of power supply 330.

Figure 4:
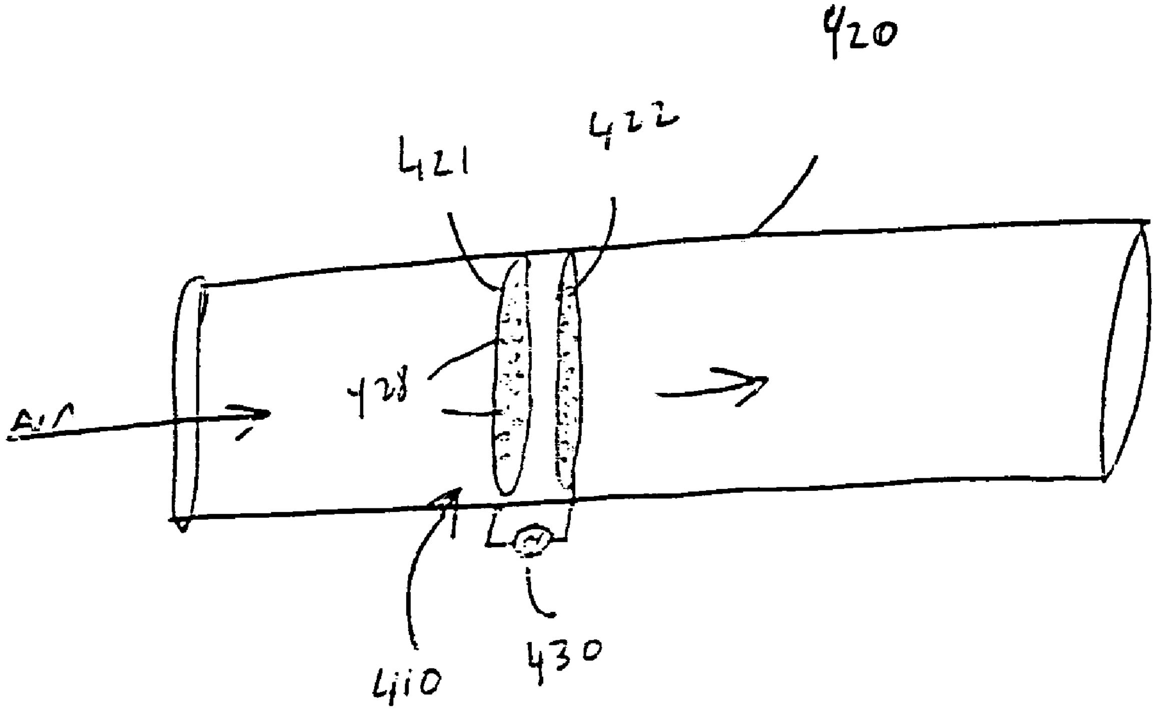
FIG. 4 shows a simplified system for electronically disinfecting air using flow through electrodes, according to another embodiment of the invention.

FIG. 4 shows another exemplary system for electronically disinfecting air 410, according to yet another embodiment of the invention. System includes a pair of electrodes 421 and 422 which includes holes or pores 428 sufficiently sized to allow air flow therethrough. Power supply 430 is connected between electrodes 421 and 422. Holes or pores in electrodes 421 and 422 increases the exposed surface area and can be used to manipulate the resulting air flow path/pattern. Although air duct 420 includes a single disinfecting system 410, multiple disinfecting systems can be used, such as stacked in a serial arrangement (not shown).

As noted above, the electrodes are generally biased using a low voltage power supply. Low voltage is used to avoid, or at least significantly reduce air ionization. The electric field generated by the applied voltage at the destruction surface provided by electrodes 121 and 122 is preferably below 2.7 MV/m. The voltage required to limit the resulting electric field to prevent air ionization depends on the system configuration, electrode shape and dielectric properties, particularly the electrode spacing in the case of a capacitive arrangement. The voltage to avoid exceeding this electric field limit is generally several hundred volts, or less, such as between 10 and 150 volts to limit on value of electric field described above.

There is generally an optimum value of electric field at which the destruction is maximum as demonstrated in the examples described below. This value depends on the electrode configuration and electrode material, as well as dielectric material when dielectric coated electrodes are used.

The power requirements for systems according to the invention is very low, generally being a fraction of a watt per square meter of disinfecting electrode surface. Using a DC bias arrangement, the power consumed is generally negligible. This power can be compared with conventional and advanced air disinfection processes which generally require 50 to 100 watts per square meter of the disinfecting surface for photocatalytic disinfection.

Products based on the invention can include relatively simple, inexpensive air disinfection devices, requiring negligible operating power. The devices can be stand alone, duct mounted or wall mounted. Such devices can be used to control indoor air pollution or mitigate pollution in an already polluted space. Since the entire electrode surface participates in the pollutant destruction, the area available for destruction is high and the electronic air disinfection device is compact.

When products based on the invention are used in building ventilation systems, they will help persons with asthma and allergy problems, and prevent the spread of disease through air. The invention may also be used in trains and airplanes. The invention can also be used to help the military to combat chemical and biological warfare. The invention can also be used to trap spreading spores such as anthrax. Such devices can be particularly effective in destroying air borne pollutants even under high biohazard concentration expected during bioterrorism.

To maintain the destruction capability of systems according to the invention at a peak level, the surfaces may be periodically regenerated in situ to remove remains of the destroyed pollutants from the surfaces. Such flexibility is not available for air disinfection systems based on filter media. Optional regeneration can be accomplished by heating the fouled surface. Heating can be accomplished using heating tape which use electrical resistance to generate heat. The heating tape can be placed in physical contact with surface to enhance the heat transfer. Another method to heat the surface is to apply high voltage across the surface and use the electrical resistance of the surface to generate the heat. The regenerating surfaces will be isolated from the air flow being disinfected. This is to avoid adverse heating of air flow. The recommended temperature of the surface during regeneration is about 450° F. Since the area for destruction is high, the necessity for regeneration is not frequent. As an alternative to regeneration, a throw away cartridge setup can be used instead. The high destruction area will still ensure high performance of the cartridge for a significant period of time.

EXAMPLES

The present invention is further illustrated by the following specific Examples, which should not be construed as limiting the scope or content of the invention in any way.

The target microorganisms for testing a system according to the invention employing electronic destruction was *Aspergillus niger* spores, which are known to be one of the most resilient microorganisms.

Figure 5:
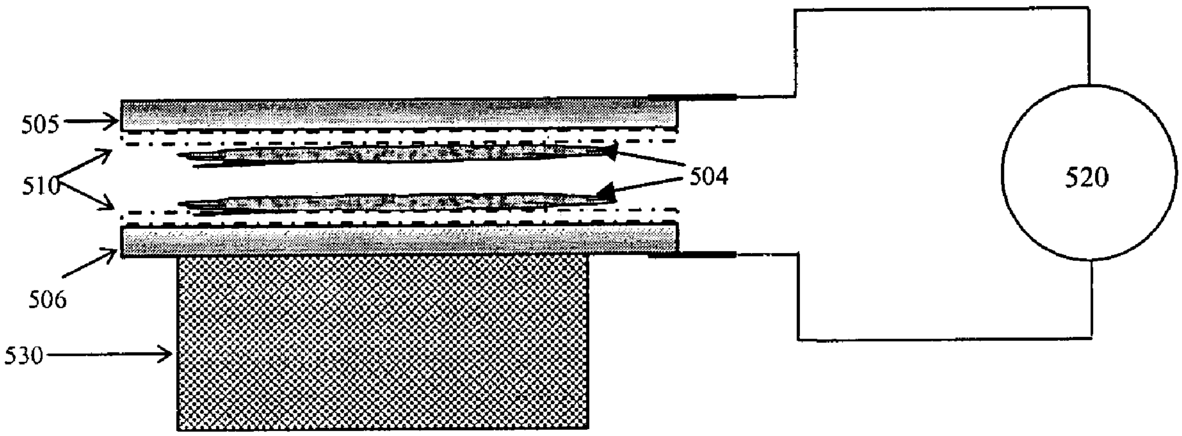
FIG. 5 shows a schematic for the system according to the invention used for electronic destruction in the Examples described herein.

The destruction experiments were designed so as to create conditions that were close to those encountered during air disinfection. FIG. 5 shows the experimental setup for electronic destruction used. The microorganisms 504 were deposited on the upper plate 505 and lower plate 506 of the capacitor formed. The capacitor plates 505 and 506 were Al and covered by dielectric ($Al_2O_3$) 510 formed from contact of the aluminum with the ambient air. An AC power supply 520 was used to bias the plates of the capacitor. The lower capacitor plate was supported by wood 530 (cellulose; an electrical insulator).

The spore concentration was diluted to 5000 cfu/ml with sterilized water and vortexed for about 1 minute to ensure uniform distribution of spores in the suspension and no spore agglomeration. 25 μml of spore suspension was deposited on each of the plates 505 and 506 with a micro syringe and uniformly spread across the plate surface using a sterilized glass rod, being careful not to push the spore suspension off the side of the plate. The microorganisms suspension was allowed to dry on the plates 505 and 506 in the dark for 24 hrs. The plates 505 and 506 were assembled to form an electrical capacitor.

The capacitor plates were 4.5 cm ×4.5 cm ×0.0127 cm thick. Layers of 3M® masking tape strips were used as spacers between the capacitor plates 505 and 506. The plate spacing distance was varied from 140 μm to 560 μm in steps of 140 μm. A test was also conducted with spacing at 0.008 m. The capacitor plates were charged by a variable AC transformer with 110 V AC input and output voltage range of 0–140 V AC, 60 Hz. The voltage was varied in steps, between (28–140 V AC). The time for the destruction runs ranged from 5 min. to 4 hrs.

After the electronic treatment both the capacitor plates 505 and 506 were placed in separate sterile petri dish and 20 mL of liquid plate count agar was poured on the plates. The spores were transferred from the plates into the agar by shaking the petri dishes for 20 seconds, and subsequently removing the plates from the agar with a sterile needle. The petri dishes were inverted on solidification of the agar and incubated at growth conditions. Finally, the colonies on each petri dish were counted to determine the percentage destruction of spores. The sum of the microbial population on both plates was taken into account to determine the percentage destruction.

Separate 4.5 cm ×4.5 cm ×0.0127 cm thick aluminum plates, with 25 μml of spore suspension dried for 24 hrs were subjected to microorganisms counts to study (a) the effect of the substrate on the microorganisms during the drying period and (b) to determine the microorganisms population on aluminum plates at the start of the electronic destruction run. The percent destruction was calculated using this count on aluminum plate as the control case.

The spore concentration in the suspension was also determined by injecting 25 μml of the spore suspension directly in the agar with micro syringe, incubating for growth and counting the colony count.

The experiments included a control to determine the relative performance of the invention as compared to conventional photocatalytic destruction using $TiO_2$ photocatalyst acting on the same batch of *Aspergillus niger*. 25 μml of spore suspension was spread and allowed to dry for 24 hrs on $TiO_2$ coated 4.5 cm ×4.5 cm ×0.0127 cm thick aluminum plate. $TiO_2$ was deposited on the aluminum plate by brush paint two coats of $TiO_2$ —water slurry and drying it before depositing the spore suspension. The plate with dried spores was exposed for 30 minutes to 350 nm UV radiations using EPR 3500 UV lamps (Southern New England Ultraviolet Company). The radiation flux at the plate surface was 50 $W/m^2$ as measured by a radiometer. The colony counts after the UV exposure were determined using the agar plating method mentioned above. All experiments were repeated at least three times.

Figure 6:
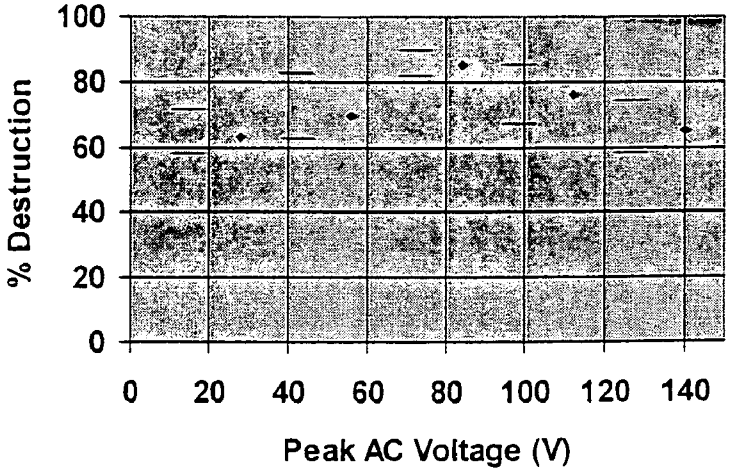
FIG. 6 shows the percent destruction of *Aspergillus niger* at different capacitor AC voltages using the system shown in FIG. 5.

The percent destruction of *Aspergillus niger* at different capacitor AC voltages is shown in FIG. 6. The capacitor plate spacing was 140 μm and the destruction time was 30 min. The destruction efficiency is seen to be at a maximum at about 84 vAC.

Figure 7:
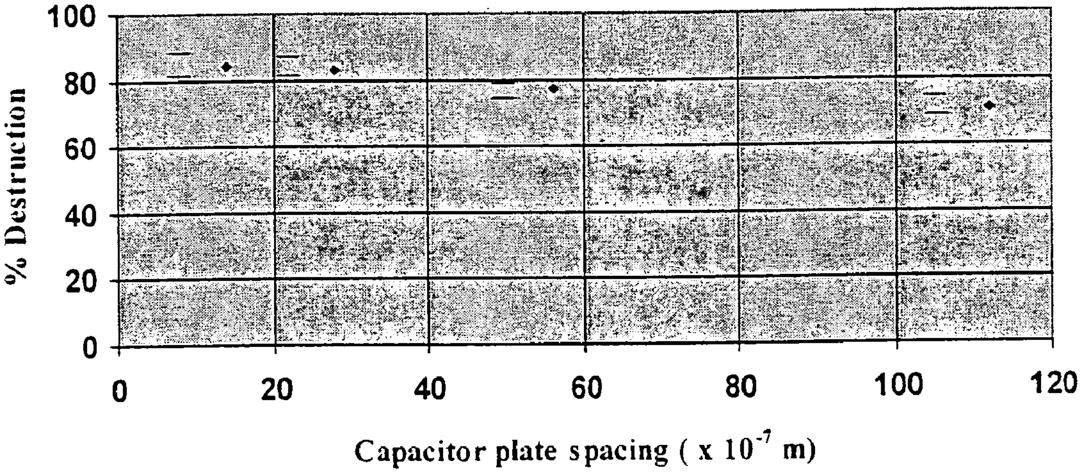
FIG. 7 shows the destruction efficiency of *Aspergillus niger* at different capacitor plate spacings using the system shown in FIG. 5.

FIG. 7 shows the destruction efficiency of *Aspergillus niger* at different capacitor plate spacings. The capacitor voltage was 84 vAC, while the destruction time was set at 30 min. The best destruction performance of 84.3% obtained was found to be at the minimum spacing used (140 μm). In comparison, photocatalytic destruction of *Aspergillus niger* was observed to be only 49% in 30 minutes.

Figure 8:
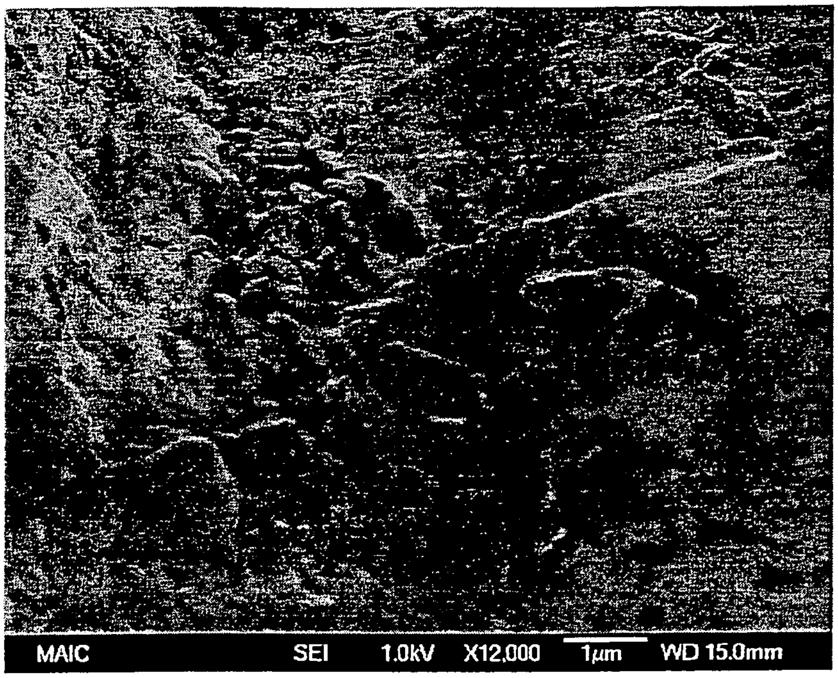
FIG. 8 shows a scanned SEM image a capacitor plate surface taken before and after electronic destruction according to the invention (Vo=84 V, 140 μm plate spacing). The *Aspergillus niger* microorganisms appear in a continuous form.
Figure 9:
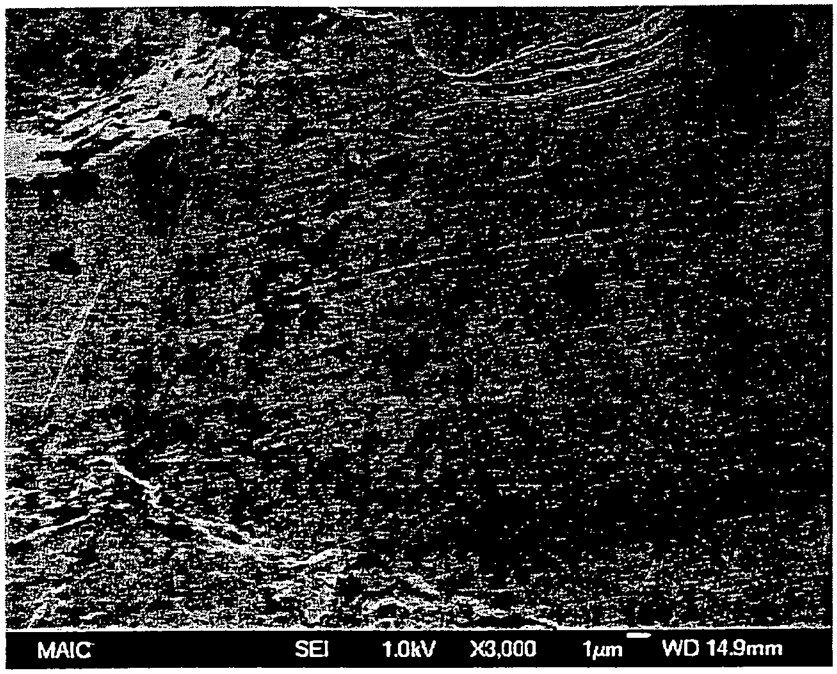
FIG. 9 shows a scanned SEM image a capacitor plate surface taken after electronic destruction according to the invention (Vo=84 V, 140 μm plate spacing) using the system shown in FIG. 5. The *Aspergillus niger* microorganisms appear to have disintegrated due to the electronic destruction process.

Scanned SEM images of the capacitor plate surface taken before and after electronic destruction (Vo=84 V, 140 μm plate spacing) are shown in FIGS. 8 and 9, respectively. The *Aspergillus niger* microorganisms which appear in a continuous form before applying the externally applied voltage (FIG. 8) appear to have disintegrated by the electronic destruction process (FIG. 9).

The Example described above demonstrates the destruction performance of a single capacitor setup with a 4.5 ×4.5 cm destruction surface. The destruction performance can be increased by increasing the destruction area, such as by using larger area capacitor plates, and/or by increasing the number of capacitors.

This invention can be embodied in other forms without departing from the spirit or essential attributes thereof and, accordingly, reference should be had to the following claims rather than the foregoing specification as indicating the scope of the invention.

What is claimed is:

1. A system for electronically disinfecting air, comprising:

a first electrode;

at least a second electrode, said fast and second electrode spaced apart from one another and having an air gap therebetween, wherein surfaces of at least one of said first and said second electrode include a dielectric layer having a thickness of 10 angstroms to 100 angstroms disposed thereon, and an electrical power supply connected between said first and said second electrode, wherein pollutants in air to be disinfected are destroyed by exposing said air to said surfaces.

2. The system of claim 1, wherein said thickness is from 30 to 100 angstroms.

3. The system of claim 1, wherein said dielectric layer is an oxide layer grown from oxidization of said electrode, wherein said oxide layer is integrated with said electrode.

4. The system of claim 1, wherein said first and said second electrode form a capacitor.

5. The system of claim 4, wherein said system comprises a plurality of said capacitors arranged in a stacked configuration.

6. The system of claim 1, wherein said first electrode is disposed outside a path of said air to be disinfected and is connected to ground, said second electrodes disposed in a path of said air to be disinfected.

7. The system of claim 6, further comprising at least one additional electrode arranged in a stacked configuration with said second electrode.

8. The system of claim 1, wherein an electric field at surfaces of said first or said second electrode under bias from said power supply is less than 2.7 Mv/m.

9. The system of claim 1, wherein at least one of said first and said second electrode is porous or include holes formed therein to allow said air to pass through.

10. The system of claim 1, wherein said power supply is an AC supply.

11. The system of claim 1, wherein said power supply is a DC supply.

12. The system of claim 1, wherein at least one of said first and second electrode has an arithmetical average surface roughness of at least 0.1 microns.

13. A method for electronically disinfecting air, comprising the steps of:

providing at least one dielectric coated electrically conductive surface, said electrically conductive surface having a dielectric coating thereon having a thickness of 10 angstroms to 100 angstroms, biasing said dielectric coated electrically conductive surface to impose charges on said dielectric coated electrically conductive surface, and passing air to be disinfected over said dielectric coated electrically conductive surface, wherein pollutants in said air are destroyed by exposure to said dielectric coated electrical conductive surface.

14. The method of claim 13, wherein an electric field at said dielectric coated surface is less than 2.7 Mv/m.

15. The method of claim 13, wherein said dielectric coated electrically conductive surface is porous or includes holes formed therein to allow said air to pass through.

16. The method of claim 13, wherein said bias is an AC bias.

17. The method of claim 13, wherein said bias is a DC bias.

18. The method of claim 13, wherein at least one of said first and second electrode has an arithmetical average surface roughness of at least 0.1 microns.

19. The method of claim 13, further comprising the step of heating said dielectric or semiconductor coated electrically conductive surface to regenerate said surface.

20. The method of claim 13, wherein said dielectric layer is an oxide layer grown from oxidization of said electrode, wherein said oxide layer is integrated with said electrode.

* * * * *